United States Patent [19]
Radomsky

[11] Patent Number: 5,942,499
[45] Date of Patent: Aug. 24, 1999

[54] METHOD OF PROMOTING BONE GROWTH WITH HYALURONIC ACID AND GROWTH FACTORS

[75] Inventor: Michael Radomsky, Mountain View, Calif.

[73] Assignee: Orquest, Inc., Mountain View, Calif.

[21] Appl. No.: 08/811,971

[22] Filed: Mar. 5, 1997

Related U.S. Application Data

[63] Continuation-in-part of application No. 08/611,690, Mar. 5, 1996, abandoned.

[51] Int. Cl.$^6$ .................................................. A61K 31/715
[52] U.S. Cl. .................................. 514/54; 514/2; 514/62; 536/53; 530/350
[58] Field of Search .................. 514/2, 54, 62; 536/53; 530/350

[56] References Cited

U.S. PATENT DOCUMENTS

| | | | |
|---|---|---|---|
| 4,394,370 | 7/1983 | Jeffries | 424/15 |
| 4,409,332 | 10/1983 | Jeffries | 435/188 |
| 4,472,840 | 9/1984 | Jeffries | 3/1.9 |
| 5,013,714 | 5/1991 | Lindstrom et al. | 514/4 |
| 5,030,457 | 7/1991 | Ng et al. | 424/486 |
| 5,100,668 | 3/1992 | Edelman et al. | 424/422 |
| 5,128,326 | 7/1992 | Balazs et al. | 514/54 |
| 5,130,418 | 7/1992 | Thompson | 530/399 |
| 5,143,662 | 9/1992 | Chesterfield et al. | 264/8 |
| 5,158,934 | 10/1992 | Ammann et al. | 514/12 |
| 5,202,311 | 4/1993 | Folkman et al. | 514/12 |
| 5,206,023 | 4/1993 | Hunziker | 424/423 |
| 5,217,954 | 6/1993 | Foster et al. | 514/12 |
| 5,266,683 | 11/1993 | Oppermann et al. | 530/326 |
| 5,294,446 | 3/1994 | Schlameus et al. | 424/489 |
| 5,302,397 | 4/1994 | Amsden et al. | 424/473 |
| 5,318,957 | 6/1994 | Cid et al. | 514/8 |
| 5,344,644 | 9/1994 | Igari et al. | 424/85.1 |
| 5,348,941 | 9/1994 | Middaugh et al. | 514/12 |
| 5,354,557 | 10/1994 | Oppermann et al. | 424/423 |
| 5,356,629 | 10/1994 | Sander et al. | 424/422 |
| 5,366,505 | 11/1994 | Farber | 623/11 |
| 5,366,964 | 11/1994 | Lindstrom et al. | 514/57 |
| 5,368,858 | 11/1994 | Hunziker | 424/423 |
| 5,368,859 | 11/1994 | Dunn et al. | 424/426 |
| 5,387,673 | 2/1995 | Seddon et al. | 530/399 |
| 5,399,352 | 3/1995 | Hanson | 424/423 |
| 5,399,583 | 3/1995 | Levy et al. | 514/410 |
| 5,409,896 | 4/1995 | Ammann et al. | 514/13 |
| 5,416,071 | 5/1995 | Igari et al. | 514/8 |
| 5,422,340 | 6/1995 | Ammann et al. | 514/12 |
| 5,425,769 | 6/1995 | Snyders, Jr. | 623/16 |
| 5,427,778 | 6/1995 | Finkenaur et al. | 424/78.08 |
| 5,428,006 | 6/1995 | Bechgaard et al. | 514/3 |
| 5,442,053 | 8/1995 | della Valle et al. | 536/55.1 |
| 5,464,440 | 11/1995 | Johansson | 623/11 |
| 5,470,829 | 11/1995 | Prisell et al. | 514/12 |
| 5,482,929 | 1/1996 | Funkunaga et al. | 514/12 |

FOREIGN PATENT DOCUMENTS

WO 91/15509  10/1991  WIPO .

OTHER PUBLICATIONS

Noda et al., 1994 "In VivoStimulation of bone formation by Transforming Growth Factor—β," Endicrinology 124:2991–4.

Pouyani and Prestwich, 1994, "Biotinylated Hyaluronic Acid: A New Tool for Probing Hyaluronate–Receptor Interactions,"Bioconjugate Chem.5:370–2.

A.A. Pilla, et al., "Non–Invasive Low–Intensity Pulsed Ultrasound Accelerates Bone Healing in the Rabbit", Journal of Orthopaedic Trauma, (1990) 4:246–253.

S. Jingushi, et al., "Acidic Fibroblast Growth Factor (aFGF) Injections Stimulates Cartilage Enlargement and Inhibits Cartilage Gene Expression in Rat Fracture Healing", Journal of Orthopaedic Trauma, (1990) 8:364–371.

Hiroshi Kawaguchi, et al., "Stimulation of Fracture Repair by Recombinant Human Basic Fibroblast Growth Factor in Normal and Streptozotocin–Diabetic Rats," Endicrinology, (1994) 135:774–781.

Urist, Marshall, "Bone: Formation by Autoinduction," Science 12, vol. 150, No. 3698, pp.893–899, Nov. 1965.

Reddi et al., "Introduction and maintenance of new bone formation by growth and differentiation factors," Annales Chirurgiae et Gynacologiae, vol. 77, pp.189–192, 1998.

Wiltfang et al., "Ectopic bone formation with the help of growth factor bFGF," Journal of Cranio–Maxillofacial Surgery, vol.24, No.5, pp.300–304, Oct. 1996.

Wozney, "Bone Morphogenetic Proteins," Progress in Growth Factor Research, vol.1, pp. 267–280, 1989.

Primary Examiner—Kathleen K. Fonda
Attorney, Agent, or Firm—Fish & Richardson P.C.

[57] ABSTRACT

A bone growth-promoting composition is provided comprising hyaluronic acid and a growth factor. The composition has a viscosity and biodegradability sufficient to persist at the site of desired bone growth for a period of time sufficient to promote the bone growth. Preferably hyaluronic acid is used in a composition range of 0.1–4% by weight and preferred growth factor is bFGF, present in a concentration range of about $10^{-6}$ to 100 mg/ml.

10 Claims, 5 Drawing Sheets

METHOD OF PROMOTING BONE GROWTH WITH HYALURONIC ACID AND GROWTH FACTORS

CROSS REFERENCE TO RELATED APPLICATIONS

This is a continuation-in-part of U.S. Ser. No. 08/611,690, filed Mar. 5, 1996, now abandoned.

BACKGROUND OF THE INVENTION

Hyaluronic acid is a naturally-occurring polysaccharide containing alternating N-acetyl-D-glucosamine and D-glucuronic acid monosaccharide units linked with beta 1–4 bonds and the disaccharide units linked with beta 1–3 glycoside bonds. It occurs usually as the sodium salt and has a molecular weight range of about 50,000 to $8 \times 10^6$.

SUMMARY OF THE INVENTION

The present invention provides a bone growth-promoting composition comprising hyaluronic acid and a growth factor such that the composition has a viscosity and biodegradability sufficient to persist at the site of desired bone growth for a period of time sufficient to promote bone growth.

Compositions comprising hyaluronic acid and a growth factor are provided which have the requisite viscosity and biodegradability.

As used herein, the term hyaluronic acid, abbreviated as HA, means hyaluronic acid and its salts such as the sodium, potassium, magnesium, calcium, and the like, salts.

By growth factors, it is meant those factors, proteinaceous or otherwise, which are found to play a role in the induction or conduction of growth of bone, ligaments, cartilage or other tissues associated with bone or joints.

In particular these growth factors include bFGF, aFGF, EGF (epidermal growth factor), PDGF (platelet-derived growth factor), IGF (insulin-like growth factor), TGF-β I through III, including the TGF-β superfamily (BMP-1 through 12, GDF 1 through 12, dpp, 60A, BIP, OF).

BRIEF DESCRIPTION OF THE DRAWINGS

FIG. 1A shows the bone thickness formed as a function of bFGF dosage; FIG. 1B shows bone thickness formation as a function of hyaluronic acid concentration;

DESCRIPTION OF THE PREFERRED EMBODIMENTS

Figure 1:
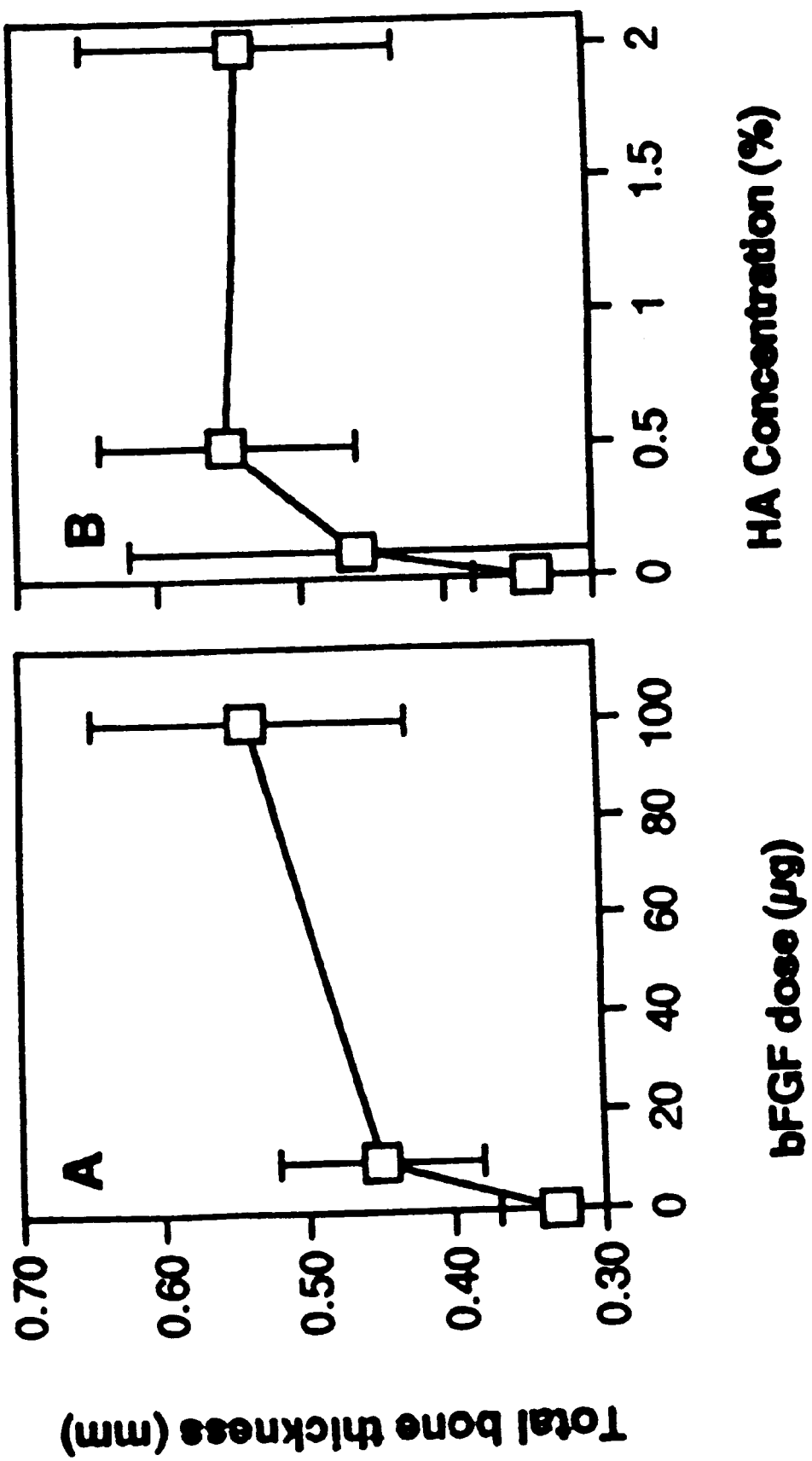
FIG. 1 is a graphical representation of experimental data set forth in example 1 below.

The processes by which the compositions and the method of their use are described in more detail.

The HA is preferably uncrosslinked having a molecular weight of 500,000 and above, typically in the range of $10^4$ to $10^7$. The bone growth-promoting compositions will typically contain from about 0.1 up to 4 percent by weight of uncrosslinked HA in an aqueous solution which also contains other solution excipients such as buffer salts, sugars, anti-oxidants and preservatives to maintain the bioactivity of the growth factor and proper pH of the composition. A composition containing from about 0.1 to 2 percent by weight of uncrosslinked HA is preferred. A typical pH of the solution will be in the range of 4 to 9, preferably about $6.0 \pm 1.0$ and most preferably about 5.0.

The growth factor will typically be present in the solution in a concentration range of about $10^6$ to 100 mg/ml of solution, particularly in the case of bFGF preferably about 0.1 to 20 mg/ml. The concentration will be dependent upon the particular bone site and application, as well as the volume of the injection and specific activity of the growth factor.

It is important for the solution used to promote the growth to have a viscosity which allows it to be injectable through a syringe or catheter, but not to be prematurely diluted by the body fluids before the bone promoting effect can be achieved. Preferably, the viscosity of the composition is within a range of 10 to $10^6$ cP and, in the case of bFGF-containing compositions, preferably about 75,000 cP.

It is also important for the composition to have a biodegradability which is sufficient to allow it to remain in place at the site of desired bone growth to effect the bone growth-promoting activity.

The composition must usually persist at the site of desired bone growth for a period from about three (3) to about thirty (30) days, typically from three (3) to about fourteen (14) days. If the composition is dispersed prematurely, the desired bone growth-promotion effect either will not occur or the formed bone will not have the desired strength.

If the composition persists at the site of desired bone growth for an excessive period, its presence at the bone site may inhibit the natural development of the bone, sometimes resulting in no bone formation at all.

The compositions are typically formed as solutions by mixing the HA and growth factor in appropriate amounts of excipients such as sodium citrate, EDTA and sucrose so that the HA and growth factor remain in solution at the desired concentration and the solution exhibits the appropriate viscosity and biodegradability. The solution may be applied to the site of desired bone growth in any convenient manner, typically by introduction through a syringe or catheter.

Administration of a bone growth composition of the present invention may be desirable to accelerate wound healing, prevent further tissue damage occurring subsequent to injury, avoid treatments that compromise the natural healing process and create optimal physical and biological conditions for healing. Sites of desired bone growth include tibia/fibula fractures; femur/humerus fractures; forearm fractures; posteriorly displaced distal radius (Colles) fracture; stress fractures including sports fractures associated with shin splints and foot injuries; vertebral compression fractures, rib fractures and clavicular fractures. Sites of desired bone growth also include pathological bone defects associated with osteoporosis, osteomalacia, hyperparathyroidism, renal osteodystrophy, and primary and metastatic cancer of the bone.

The invention is described in more detail in the following examples, which are provided by way of illustration and are not intended to limit the invention set forth in the claims.

EXAMPLE 1

Sodium hyaluronate (Genzyme, MW $2 \times 10^6$, sterile, viscosity in 1% solution of 6500 cP), bFGF (Scios-Nova, 4.3 mg/ml solution (pH 5) in 9% sucrose, 20 mM sodium citrate and 1 mM EDTA) were mixed. The formulations were formed by mixing sterile-filtered solutions of bFGF and other excipients (sodium citrate, water, etc.) with the appropriate amount of solid, sterile HA. The HA was dispersed quickly by repeated back and forth syringing to prevent the formation of large aggregates of particles. Formulations were prepared aseptically and administered in prefilled 1 ml plastic syringes with 21 G needles into male Sprague-Dawley rats (8–9 weeks old, 160–180 grams), which were anesthetized with acepromazine, xylazine and ketamine. A 5–10 millimeter incision was made laterally in the skin at the back of the neck to locate the intersection of the sagittal and lambdoid sutures. Fifty microliters of the test formulation was injected with a 21 G needle between the periosteum and parietal bone. The animals were euthanized 14 days following treatment.

Tissues for histological analysis were fixed in 10% neutral buffered formalin. Tissues were decalcified for at least 2 hours in formic acid (RapidBone Decal) with constant, gentle agitation. Samples were dehydrated and infiltrated with paraffin. Specimens were then embedded in a cross-sectional plane and sectioned at 5 μm. Sections were stained with hematoxylin and eosin for histological analysis. New bone formation was scored on a scale of 0 to 4 as shown in Table 1.

| Score | Description of New, Woven Bone Formation |
|---|---|
| 0 | None; no new, woven bone |
| 1 | Trace/patchy areas of woven bone |
| 2 | Areas of both continuous and patchy woven bone |
| 3 | Thin, continuous woven bone (<50% of original parietal bone) |
| 4 | Thick, continuous woven bone (>50% of original parietal bone) |

The total thickness of the parietal bone was measured similar to the method of Noda et al., *Endocrinology*, 124:2991–4, 1989. A photograph of each histology section was taken 2 to 3 mm lateral to the sagittal suture (the approximate midpoint between the sagittal suture and the edge of the section). Three bone thickness measurements of total bone were taken at the left, middle, and right side of the photograph and scaled to determine total bone thickness. Both dense cortical bone and new, woven bone were included in the measurement.

In all groups the response to each treatment was consistent between animals in the same treatment group. Qualitatively, the groups of animals treated with all of the bFGF/HA gel formulations exhibited new bone formation while placebo treated and growth control animals show minimal or no new bone formation (table 2). It was apparent that only small differences existed between the bFGF/HA formulations examined in this study. However, there did appear to be a dose response effect. (FIG. 1A, 1B).

| Formulation | | Total number of animals with a bone formation score of: | | | | |
|---|---|---|---|---|---|---|
| bFGF Dose (μg) | HA Conc. (%) | 0 | 1 | 2 | 3 | 4 |
| 100 | 2 | | | | 2 | 2 |
| — | — | | | | | |
| 100 | 2 | | | | 2 | 2 |
| — | — | | | | | |
| 10 | 2 | | | | 2 | 2 |
| 100 | 0.5 | | | 1 | 2 | 1 |
| 100 | 0.1 | | 2 | | | |
| — | 2 | 2 | | | | |
| sham operation | | 3 | | | | |
| growth control | | 2 | | | | |

Table 3 shows the total bone thickness of the rat calvaria after receiving different formulations by subperiosteal injection. All formulations containing bFGF and HA exhibited new bone formation. The first two entries in table 3 represent replicate experiments. Replicate groups of animals receiving 100 μg bFGF in a 2% HA gel had a total parietal bone thickness of 0.49±0.10 mm in the first study and 0.59±0.12 mm in the second study, a 17% difference. However, the total bone thickness of both groups was qualitatively and quantitatively significantly different than control. All formulations containing 100 μg of bFGF and HA had at least a 61% increase in new bone formation compared to animals receiving no treatment.

FIG. 1A and 1B show the effect of bFGF and HA concentration on total bone thickness. As the dose of bFGF increase from 10 to 100 μg, the total bone thickness increases 20% from 0.45 to 0.54 mm. As the concentration of HA increases, an increase in total bone formation is seen until a maximum increase in bone formation is observed near 0.5% HA; increasing the concentration of HA above 0.5% does not result in an additional increase in new bone formation elicited by bFGF in this model (FIG. 1B).

TABLE 3

The total bone thickness of a section of the rat calvaria 2 mm anterior of the lambda and 2 to 3 mm lateral to the parietal suture 14 days following treatment. Bone thickness is the average of 3 measurements per animal. n is the number of replicate animals, and the percent increase represents the fractional increase over growth control.

| Formulation | | | Total Bone Thickness | |
|---|---|---|---|---|
| bFGF Dose (μg) | HA Conc. (%) | n | mean ± SD (mm) | Percent Increase |
| 100 | 2 | 4 | 0.49 ± 0.10 | 75% |
| 100 | 2 | 4 | 0.59 ± 0.12 | 111% |
| 10 | 2 | 4 | 0.45 ± 0.07 | 61% |
| 100 | 0.5 | 4 | 0.55 ± 0.09 | 96% |
| 100 | 0.1 | 4 | 0.46 ± 0.16 | 64% |
| 100 | — | 2 | 0.34 ± 0.04 | 21% |
| — | 2 | 4 | 0.33 ± 0.04 | 18% |
| sham operation | | 3 | 0.24 ± 0.04 | -14% |
| growth control | | 2 | 0.28 ± 0.01 | 0% |

It was thus shown that a single, subperiosteal injection of 100 μg of bFGF in an HA gel showed significant qualitative and quantitative effect on intramembranous bone formation over controls. Fourteen days following administration, up to 111% new bone is formed at the site of injection in animals treated with 100 μg of bFGF in HA gels. Placebo and control groups all had less than a 18% increase in bone thickness 14 days following injection. As the dose of bFGF increase from 10 to 100 μg, the total bone thickness increases 20% from 0.45 to 0.54 mm. Increasing the concentration of HA above 0.5% does not result in an additional increase in new bone formation elicited by bFGF in this model.

EXAMPLE 2

Figure 2:
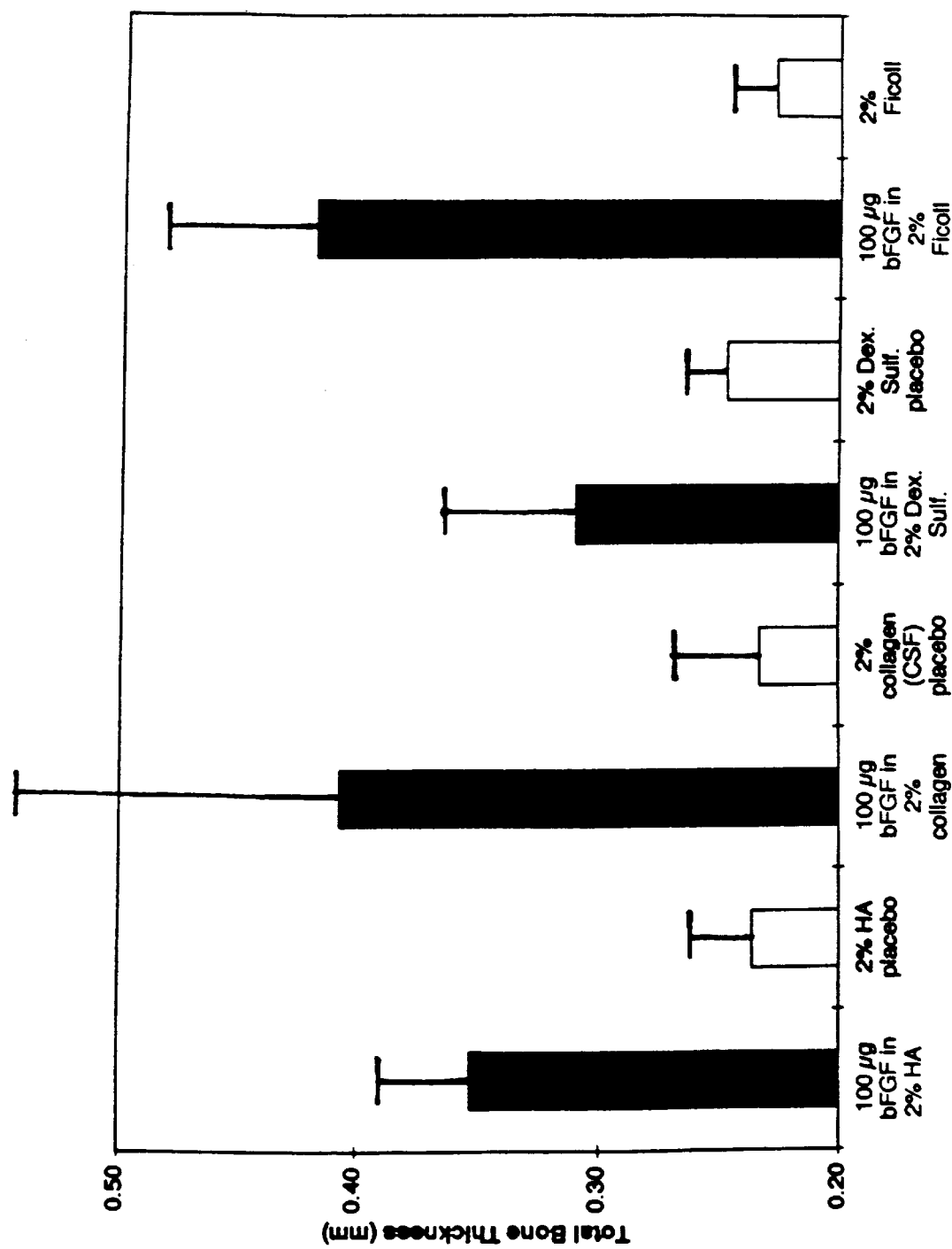
FIG. 2 is a graphical representation of the experimental data set forth in Example 2 below.

The tests described in Example 1 were conducted using 8 different formulations. The bFGF was used in combination with hyaluronic acid as compared to 7 other compositions wherein bFGF was used with other carriers or the carriers were used alone as placebos. The results are shown below and are summarized in FIG. 2 and Table 4.

TABLE 4

The total number of animals with a bone formation score

| Formulation | Total number of animals with a bone formation score of: | | | | |
|---|---|---|---|---|---|
| | 0 | 1 | 2 | 3 | 4 |
| 100 μg bFGF in 2% HA | | | | 3 | 1 |
| 2% HA placebo | 4 | | | | |
| 100 μg bFGF IN 2% collagen (CSF) | | | 2 | 2 | |
| 2% collagen (CSF) placebo | 3 | 1 | | | |
| 100 μg bFGF in 2% Dex. Sulf. | 1 | 1 | | 2 | |
| 2% Dex. Sulf. placebo | 4 | | | | |
| 100 μg bFGF in 2% Ficoll* | | | | 3 | 1 |
| 2% Ficoll placebo | 4 | | | | |

*An uncharged polysaccharide.

EXAMPLE 3

Formulations of sodium hyaluronate (2%) and bFGF (4 mg/ml) were prepared as in Example 1 for administration to a fracture site in rabbits. A formulation was also prepared containing 4 mg/ml bFGF, 6 mg/ml rabbit fibrinogen, 0.2 mg/ml aprotinin, and other excipients to maintain pH and stability. This fibrinogen formulation was similar to a previously published composition used for fracture repair[1]. A 1 mm cut in the fibula mid-diaphysis was surgically created in New Zealand White rabbits to model a bone fracture. This experimental method has previously been utilized to examine the healing of fractures in rabbits[2]. Animals were treated with 50 μL of the HA/bFGF formulation, 50 μL of the fibrinogen/bFGF formulation, or remained untreated.

Figure 3:
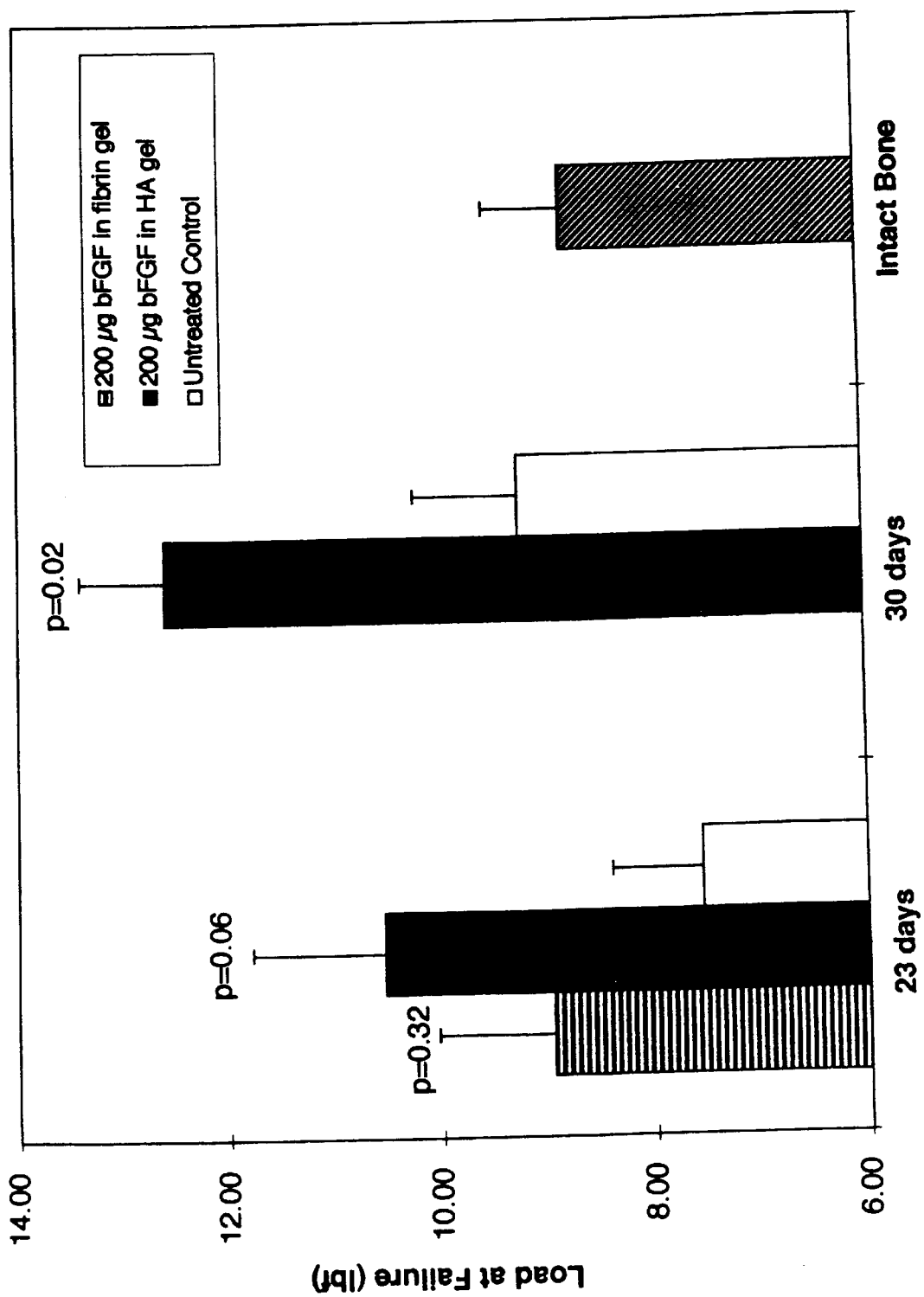
FIG. 3 is a graphical representation of the load at failure of healing rabbit fibula after 23 and 30 days following treatment according to Example 3.
Figure 4:
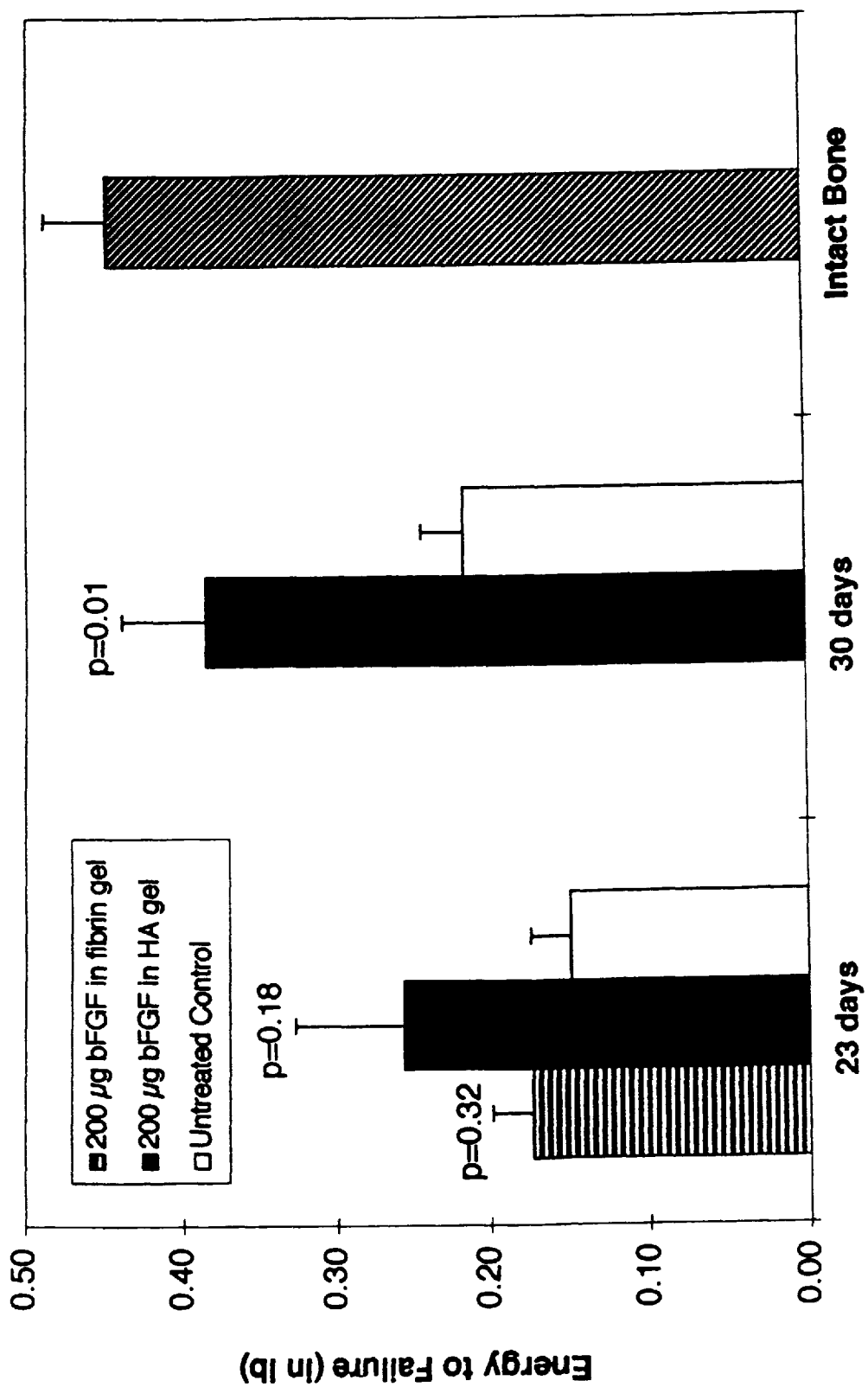
FIG. 4 is a graphical representation of the energy to failure (in pounds) of healing rabbit fibula after 23 and 30 days following treatment according to Example 3.

The mechanical strength of 10 healed fibula per treatment group was measured by a four point bending technique 23 days following treatment. FIG. 3 illustrates the load at failure for untreated, HA/bFGF treated, and fibrinogen/bFGF treated fibulae. The HA/bFGF treated fibulae were 53% stronger than untreated control, while the fibrin/bFGF treated fibulae were 30% stronger than untreated control. FIG. 4 shows the energy to failure for all three treatment groups. By this measurement, the HA/bFGF treated fibulae were 43% stronger than untreated control, while the fibrin/bFGF treated fibulae were 3% weaker than untreated control.

In addition, the mechanical strength of 10 untreated fibulae and 10 HA/bFGF treated fibulae was measured 30 days following treatment. FIG. 3 shows that the load at failure is 36% higher in HA/bFGF treated animals over control and that this difference is statistically significant (p=0.02). FIG. 4 indicates that the energy to failure is 79% higher in the HA/bFGF versus control and that this difference is statistically significant (p=0.01). FIGS. 3 and 4 also show that the strength of HA/bFGF treated fibulae return to the strength of intact bone more quickly than untreated fibulae, indicating accelerated bone healing.

1. Hiroshi Kawaguchi, et al., Stimulation of Fracture Repair by Recombinant Human Basic Fibroblast Growth Factor in Normal and Streptozotocin-Diabetic Rats, *Endocrinology*, 135:774–781, 1994.

2. A. A. Pilla, et al., Non-invasive Low-intensity Pulsed Ultrasound Accelerates Bone Healing in the Rabbit, *Journal of Orthopaedic Trauma*, 4:246–253, 1990.

EXAMPLE 4

The method in Example 1 was used to compare total bone formation of the HA/bFGF formulation in Example 1, the fibrin/bFGF formulation in Example 3, and a bFGF in an aqueous sucrose/citrate buffer formulation. 100 μg of bFGF in 50 μL each formulation was administered by subperiosteal injection, and animals were sacrificed 7 and 14 days post-administration. In addition, animals receiving no treatment were used as controls.

In each of the four groups the response to each treatment was very consistent between animals. At 7 days all bFGF treated animals show intramembranous bone that has formed on the calvarium in response to the bFGF. The control animals show minimal or no new bone formation. Qualitatively, the group of animals treated with bFGF in a HA gel had more new bone formation than in any of the other bFGF formulations. In the 14 day specimens, the difference in the amount of bone formation in the bFGF/HA gel treated animals was even more apparent. While new bone formed in all bFGF treated animals, it was readily apparent that a much thicker bone mass had formed in the bFGF/HA gel treated animals than in any other treatment group.

Figure 5:
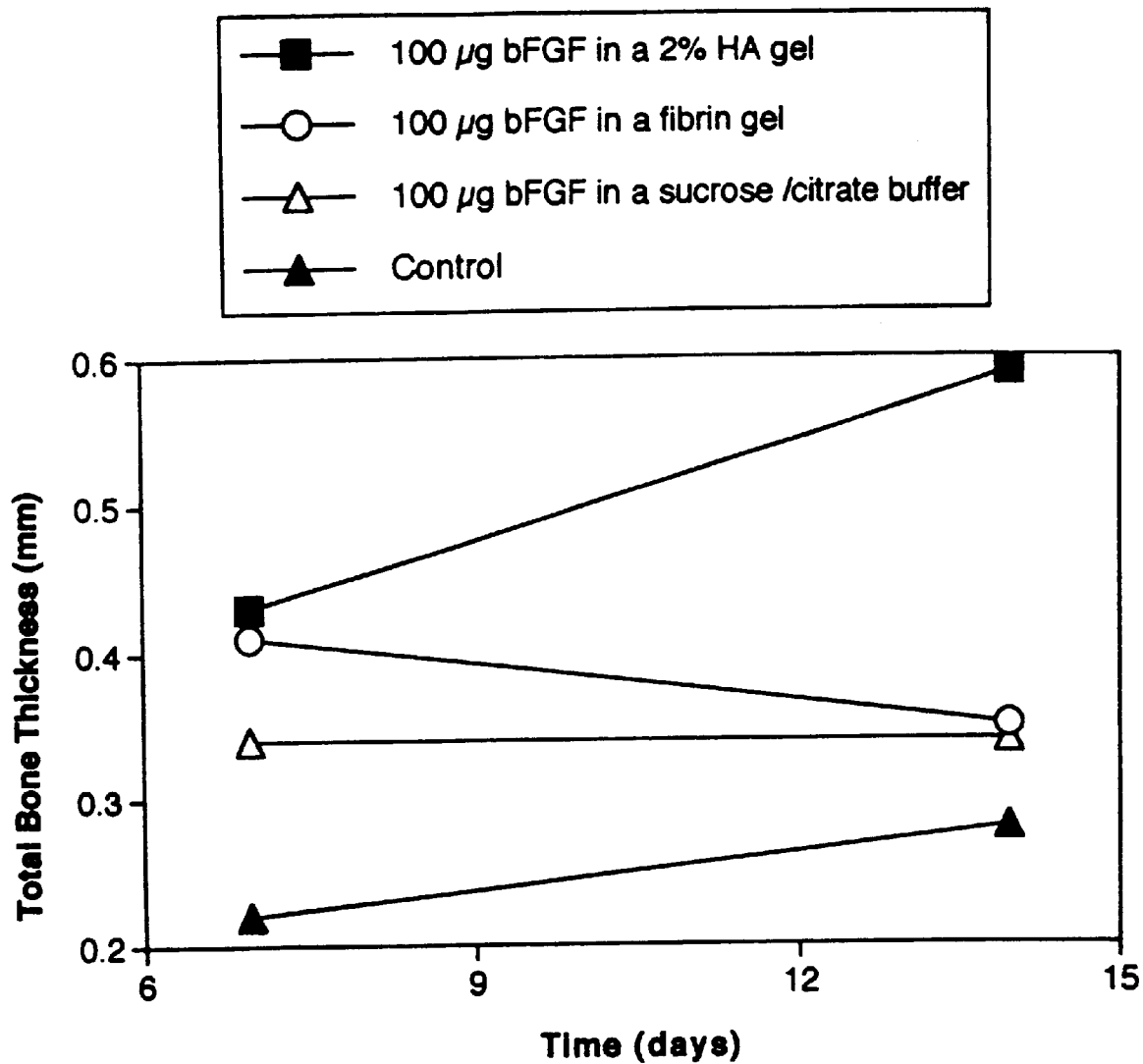
FIG. 5 is a graphical representation of the bone thickness data in rats following treatment according to Example 4.

FIG. 5 shows the quantitative results of the bone thickness measurement. The thickness 7 days after treatment is 95% thicker in the animals administered 100 μg of bFGF in a 2% HA gel than in animal receiving no treatment (i.e. control). The other bFGF treated groups showed a 86 and 55% increase in bone formation by treatment with bFGF in a fibrin gel and bFGF in an aqueous citrate buffer, respectively.

At 14 days 111% new bone is formed in animals treated with 100 μg of FGF in an HA gel (FIG. 5). Other bFGF treated groups had only a 25 and 21% increase in bone formation in rats treated with bFGF in a fibrin gel and bFGF in an aqueous citrate buffer, respectively.

EXAMPLE 5

The effect of the molecular weight of hyaluronic acid in basic fibroblast growth factor (bFGF) formulations on intramembranous bone formation was examined by subperiosteal injection to the rat parietal bone.
Materials and Methods
The HA with a molecular weight of 760 to 2300 KDa (from Genzyme and Lifecore Biomedical) was used to prepare formulations. The BFGF was provided (Scios-Nova) as a frozen solution (4.3 mg/ml) in 9% sucrose, 20 mM sodium citrate, and 1 mM EDTA adjusted to pH 5.0. Other reagents (sucrose, sodium citrate, EDTA) were purchased from Sigma.

Formulations were prepared by mixing a sterile filtered solution of bFGF (2 mg/ml) with the appropriate amount of HA (20 mg/ml). The solution and carrier initially were in separate syringes connected by a stopcock. The formulation was mixed by repeated back and forth syringing. Formulations were prepared aseptically and administered in prefilled 1 ml plastic syringes with a 21 G needle.

Male Sprague-Dawley rats (8–9 weeks old, 160–180 g) were anesthetized with a mixture of acepromazine, xylazine, and ketamine. A small incision (5–10 mm) was made laterally in the skin at the back of the neck. The intersection of the sagittal and lambdoid sutures was located, and 50 $\mu$L of each formulation was injected with 21 G needle on the left side between the periosteum and parietal bone. Fourteen days following treatment animals were euthanized by $CO_2$ asphyxiation.

Tissues for histological analysis were fixed in 10% neutral buffered formalin. Tissues were decalcified for at least 2 hours in formic acid (RapidBone Decal) with constant, gentle agitation. Samples were dehydrated and infiltrated with paraffin. Specimens were then embedded in a cross-sectional plane and sectioned at 5 $\mu$m. Sections were stained with hematoxylin and eosin for histological analysis. New bone formation was scored on a scale of 0–4. A score of 0 represented no new woven bone; a score of 1 represented trace or patchy areas of woven bone; a score of 2 represented larger areas of patchy bone formation; a score of 3 represented thin, continuous woven bone (<50% of original parietal bone) and a score of 4 represented thick, continuous woven bone (>50% of original parietal bone).

Bone Thickness Measurement

The total thickness of the parietal bone was determined at the site of injection. A photograph of each histology section was taken 2 to 3 mm lateral to the sagittal suture (the approximate midpoint between the sagittal suture and the edge of the section). Three bone thickness measurements of total bone were taken at the left, middle, and right side of the photograph and scaled to determine total bone thickness. Both dense cortical bone and new, woven bone were included in the measurement.

Results

Qualitatively, all groups of animals treated with bFGF exhibited some new bone formation while HA only gel treated animals and controls show minimal or no new bone formation. Histologically, bFGF treated animals showed the presence of new, woven bone and mature lamellar bone. At the injection site a marked layer of new woven bone had formed superficial to the more mature underlying bone. Occasionally, the woven bone is present on the right side, but is not present to the same extent that is seen on the left side. The new woven bone show normal reversal lines, marrow spacing and general staining characteristics. Most animals in these groups received a bone formation score of 3 (28/30), while two animals received the maximum score of 4. Above the woven bone, there is an area of adipose and fibrous tissue in close approximation to the new woven bone and appear normally configured. No areas show foci of chronic inflammatory cells which would be an indication of antigenic potential of the HA/bFGF formulation.

The HA gel treated animals showed no or very little new bone formation, and most animals received a bone formation score of 0 (26/30). Three of 30 animals had a bone formation score of 1 while a single animal had a bone formation of 3. The new bone formation may be a result of elevation of the periosteum during the surgical procedure. No abnormalities are observed in any part of the tissue, and there is no indication of antigenic potential in any of the HAs examined.

Animals receiving no surgery and no treatment showed no new bone formation and all six animals received a bone formation score of zero. This group was very similar to the groups receiving HA gel, except that no new bone formed as a result of elevation of the periosteum. The specimens consisted of mature bone in which normal osteocytes are present in lacunae, and marrow spaces were seen. Small amounts of fine fibrous tissue are present superficially to the bone tissue in all sections.

With respect to bone thickness, FGF treated groups had a 68–100% increase in bone thickness over the growth control. The animals treated with bFGF in a gel formed from Lifecore's highest molecular weight HA available had the largest increase in bone thickness (100%). There was a slight effect of molecular weight on bone formation. As the molecular weight of HA increased, the amount of new bone formed also increased. This increase in bone formation could be due to the increase in viscosity of the formulation. As the viscosity increased, it became a larger diffusional barrier for the FGF maintaining it at the site locally for a longer period. The longer residence time of HA then results in more bone formation.

EXAMPLE 6

This Example addresses the local distribution and persistence of hyaluronic acid following subperiosteal injection of an HA+bFGF gel. This study examined the proliferation of the periosteum, new bone formation, and the local distribution and persistence of hyaluronic acid (HA) following subperiosteal injection of an HA gel containing basic fibroblast growth factor (bFGF). The periosteal thickness at 3 days and bone thickness at 10 days was determined by histologic evaluation.

MATERIALS AND METHODS

Materials

Sodium hyaluronate (HA) was purchased from Lifecore Biomedical (Chaska, Minn., 1300 kDa). bFGF was provided by Scios-Nova as a frozen solution (4.3 mg/ml) in 9% sucrose, 20 mM sodium citrate, and 1 mM EDTA adjusted to pH 5. Formulation buffer reagents (sucrose, sodium citrate, EDTA, BSA) were purchased from Sigma. Adipic dihydrazide (AD) and 1-ethyl-3[3-(dimethylamino)propyl] carbodiimide (EDC) were purchased from Aldrich. Sulfo-NHS-Biotin (SNB), 2-(4' hydroxyphenylazo) benzoic acid (HABA), a 3,3' diamino benzidine tetrahydrochloride (DAB) metal enhanced substrate kit, and an avidin-horseradish peroxidase (Av-HRP) conjugate were purchased from Pierce. Tween 20 was purchased from Baker.

Biotinylation

The HA-Biotin (HA-Bi) conjugate was prepared by a two step reaction. Hydrazido-HA was synthesized followed by preparation of HA-Bi according to the method of Pouyani and Prestwich, *Bioconjugate Chem.* 5:370–372 (1994). Hydrazido-HA was prepared by dissolving 200 mg of HA in 50 ml of water. AD (3.5 g) was added to the HA solution and the pH was adjusted to 4.75 with 0.1 N HCl. EDC (382 mg) was added to the solution to begin the reaction. The pH was monitored periodically and maintained at 4.75 by the addition of 0.1 N HCl. The reaction was stopped after 4 hours (at this point no further increase in pH was detected) by neutralization to pH 7 with 1 N NaOH. This product was dialyzed for 72 hrs (Specta/Por, 6000 to 8000 MW cutoff) and then lyophilized for 48 hours.

The HA-Bi conjugate was prepared by dissolving 15 mg of Hydrazido-HA in 1.5 ml of 0.1 M NaHCO3. The SNB (50 mg) was added to begin the reaction. The solution was stirred with a small magnetic stir bar for 20 hours at room temperature. The solution was dialyzed for 72 hours and then lyophilized for 48 hours. The degree of substitution was determined by a displacement assay according to the manufacturer's protocol (Pierce). Briefly, 900 μL of avidin-HABA reagent was placed in a 1 ml cuvette. The absorbance at 500 nm was compared to the absorbance of a solution of 900 μL of Avidin-HABA plus 100 μL of a 1 mg/ml HA-Biotin solution. The average degree of substitution was 30 moles of repeating disaccharide unit per mole of biotin.

Formulation

Formulations were prepared by mixing a sterile-filtered solution of bFGF with solid HA as described in Table 5. The formulation was mixed by repeated back and forth motion of two syringes connected by a stopcock. Formulations were prepared aseptically and administered in prefilled 1 ml plastic syringes with a 21 G needle.

TABLE 5

HA-Bi formulations

| Component | Formulations | | |
|---|---|---|---|
| | HA-Bi + bFGF | HA + bFGF | HA-Bi |
| basic fibroblast growth factor (bFGF) | 4 mg/ml | 4 mg/ml | — |
| Hyaluronic Acid-Biotin Conjugate (HA-Bi) | 4 mg/ml | — | 4 mg/ml |
| Hyaluronic Acid (HA) | 16 mg/ml | 20 mg/ml | 16 mg/ml |
| Sucrose | 9% | 9% | 9% |
| Sodium Citrate | 20 mM | 20 mM | 20 mM |
| EDTA | 1 mM | 1 mM | 1 mM |

Animal Model

Male Sprague-Dawley rats (6–7 weeks old, 160–180 g, n=5 per group) were anesthetized with a mixture of acepromazine, xylazine, and ketamine. A small incision (5–10 mm) was made laterally in the skin at the back of the neck. The intersection of the sagittal and lambdoid sutures was located, and 50 μL of each formulation was injected on the left side with a 21 G needle between the periosteum and parietal. Fourteen days following treatment animals were euthanized by $CO_2$ asphyxiation.

Histology

Tissues for histological evaluation were fixed in 10% neutral buffered formalin then decalcified in a 13 to 15% solution of EDTA with constant, gentle agitation. Samples were dehydrated and infiltrated with paraffin. Specimens were then embedded in a cross-sectional plane and sectioned at 4 μm. Two sections were prepared for each specimen and were stained with hematoxylin and eosin (H&E) or stained for HA with Bi:Av-HRP histochemistry by the following method. Tissue sections were incubated for 30 min in blocker solution (1% BSA/0.05 Tween in PBS) followed by a 60 min incubation in detecting conjugate solution (1 μg/ml Avidin-HRP in 1% BSA/0.05% tween in PBS). These tissue sections were then placed in wash solution (0.05% tween in PBS) for 5 min. The wash in PBS/tween was repeated 5 times with fresh solution. A metal enhanced DAB kit was utilized to stain for the HA-Bi:Av-HRP complex. Five minutes after applying the DAB substrate the sections were rinsed in water. A black precipitate formed in the presence of the complex. Finally, these sections were counterstained with hematoxylin (H) for cellular detail.

Periosteum and Bone Thickness Measurement

The total thickness of the periosteum and parietal bone was determined at the site of injection. A photograph of each histology section was taken 2 to 3 mm lateral to the sagittal suture (the approximate midpoint between the sagittal suture and the edge of the section). Three thickness measurements were taken at the left, middle, and right side of the photograph and scaled to determine total bone thickness or periosteum thickness. Tissue with similar staining characteristics and cell morphology to normal periosteum was included in the periosteum thickness. Both dense cortical bone and new, woven bone were included in the bone thickness measurement.

Results

Animals treated with bFGF in an HA gel showed an increase in the thickness of the periosteum at 3 days and significant woven bone formation at 10 days. Animals treated without bFGF showed limited periosteum thickening and bone formation. HA-Bi was detected in the tissues immediately adjacent to the thickened periosteum at 3 days and the newly formed bone at 10 days.

For HA-Bi, Administration at 3 Days

At the injection site a distinct mass of HA was present above the periosteum. There was a portion of the periosteum elevated from the lamellar bone from the surgical trauma. In the area stained for HA, there was a localized area of fibrous tissue and a non-specific cellular infiltrate in which lymphocytes and degenerating cells were evident. The surrounding tissue consisted of fine fibrous tissue.

HA-Bi, Administration at 10 Days

The HA-Bi treated animals showed normal lamellar bone with an area of non-specific fibrous tissue resembling granulation tissue above it. This area contained lymphocytes, fine blood vessels, fat cells and a few fragments of unstained material. The brownish-black peroxidase stain was within the dense fibrous tissue superficial to the calvarium on the left side. The HA was distributed non-specifically within the fibrous tissue.

For HA-Bi+bFGF Administration at 3 Days

At the injection site there was hyperplasia of the periosteal layer overlaying the pre-existing lamellar bone. Quantitatively, the periosteum in HA-Bi+FGF treated animals was 403% greater than animals treated only with HA-Bi gel. A mass of vascularized, exuberant fibrous tissue was present above the thickened periosteum. Within this fibrous tissue, fat cells were present and a non-specific inflammatory cell infiltrate containing some polymorphonuclear leukocytes, histocytes and plasma cells were present. The residual HA extended across the midline suture and appeared to be undergoing encapsulation. These samples showed a concentration of brownish-black stained material (i.e. HA) mainly concentrated within the confines of the encapsulated tissue. More of this material appeared to be non-specifically retained within a fibrous network and some appeared to be non-specifically accumulated within the cytoplasm of local histocytes.

HA-Bi+bFGF, Administration at 10 Days

The injection site showed that the preexisting calvarial lamellar bone was covered by a thick layer of maturing woven bone which was normal in structure and staining qualities. The total bone thickness was 70% greater in animals treated with HA-Bi+FGF than in animals receiving HA-Bi gel. This new bone typically extended just beyond the midline suture onto the right side of the calvarium. DAB staining for HA was seen in the superficial layers of the fibrous tissue proliferation surrounding the newly formed woven bone. The peroxidase staining indicated that the HA was typically present in tissues adjacent to newly formed bone. Above the woven bone a fibro-periosteal layer was present. Superficial to this there was an extensive area of fine fibrous tissue which was vascularized and contained adipose cells. Some lymphocytes, plasma cells, and histocytes were also present in this well developed area which was limited by a thin fibrous tissue layer.

HA+bFGF Administration at 3 Days and 10 Days

Qualitatively and quantitatively conjugating biotin to HA had no effect on the biological response to the formulation (Table 6). The periosteum and bone thicknesses of the HA+FGF treated group were not statistically different from the HA-Bi+FGF treated group (p>0.05), but were significantly different than HA-Bi treated controls (p<0.001). Histologically, the animals treated with HA+bFGF with no biotin were similar to the HA-Bi+bFGF except that there were no areas that were stained brownish-black from the DAB substrate. These areas were not expected to stain because of the absence of biotin. A few cells did stain positively because of the presence of endogenous peroxidase activity.

TABLE 6

The periosteum and bone thickness of the three groups examined in this study

| Treatment | Periosteum thickness, 3 days ($\mu$m) | | Total bone thickness, 10 days ($\mu$m) | |
| --- | --- | --- | --- | --- |
| | mean ± SD | % greater than HA-Bi gel | mean ± SD | % greater than HA-Bi gel |
| HA-Bi + bFGF | 53 ± 3 | 403% | 464 ± 21 | 70% |
| HA + bFGF | 47 ± 2 | 341% | 420 ± 16 | 54% |
| HA-Bi gel | 11 ± 1 | 0% | 272 ± 6 | 0% |

The administration of an HA+bFGF gel by subperiosteal injection had a significant effect on the proliferation of the periosteum and active bone formation. Three days after administration, the periosteum was nearly 5 fold thicker than control. In addition, 10 days following administration the parietal bone thickness was 70% greater than control in HA/bFGF treated rats. The HA carrier in the formulations examined here directs the formation of new bone by placement of the material; HA is seen in areas of active bone formation. Following injection of HA+bFGF, the HA provides a reservoir of bFGF adjacent to the site of new bone formation.

In addition to providing site directed release of bFGF, HA has biological properties that appear to support an environment to promote bone formation. HA may have a synergistic effect with FGF.

The foregoing disclosure and description of the invention are illustrative and explanatory thereof and various changes in the size, shape and materials as well as in the details of the preferred embodiment may be made without departing from the spirit of the invention.

What is claimed is:

1. A composition for treatment of diseased, injured or abnormal bone comprising an effective amount of a mixture of a growth factor and hyaluronic acid sufficient to enhance bone growth rate and magnitude and having a sufficient viscosity and biodegradability to persist upon application at an orthotopic or intraosseous site of desired bone growth for a period of time sufficient to enhance said bone growth rate and magnitude.

2. A composition according to claim 1 wherein said hyaluronic acid is uncrosslinked.

3. A composition according to claim 1 wherein said composition comprises 0.1 to 4% by weight of hyaluronic acid in solution.

4. A composition according to claim 1 wherein said growth factor comprises bFGF.

5. A composition according to claim 4 wherein said bFGF is present in said composition in a range of about $10^{-6}$ to 100 mg/ml of said composition.

6. A method of treating diseased, injured or abnormal bone at an orthotopic or intraosseous site of desired bone growth comprising the step of applying to said site a composition comprising an effective amount of a mixture of hyaluronic acid and a growth factor sufficient to enhance bone growth rate and magnitude and having a sufficient viscosity and biodegradability to persist at said site for a period of time sufficient to enhance said bone growth rate and magnitude.

7. A method according to claim 6 wherein said hyaluronic acid is uncrosslinked.

8. A method according to claim 6 wherein said hyaluronic acid in said composition comprises about 0.1–4% by weight of said composition.

9. A method according to claim 6 wherein said growth factor comprises bFGF.

10. A method according to claim 9 wherein said bFGF is present in a range of about $10^{-6}$ to 100 mg/ml in said composition.

* * * * *

(12) REEXAMINATION CERTIFICATE (4806th)
United States Patent
Radomsky

(10) Number: US 5,942,499 C1
(45) Certificate Issued: Jul. 8, 2003

(54) METHOD OF PROMOTING BONE GROWTH WITH HYALURONIC ACID AND GROWTH FACTORS

(75) Inventor: Michael Radomsky, Mountain View, CA (US)

(73) Assignee: Orquest, Inc., Mountain View, CA (US)

Reexamination Request:
No. 90/006,055, Jul. 10, 2001

Reexamination Certificate for:
Patent No.: 5,942,499
Issued: Aug. 24, 1999
Appl. No.: 08/811,971
Filed: Mar. 5, 1997

Related U.S. Application Data

(63) Continuation-in-part of application No. 08/611,690, filed on Mar. 5, 1996, now abandoned.
(51) Int. Cl.⁷ .............................................. A61K 31/715
(52) U.S. Cl. ................................ 514/54; 514/2; 514/62; 536/53; 530/350
(58) Field of Search ................................ 514/2, 54, 62; 536/53; 530/350, 326; 623/11, 16, 18

(56) References Cited

U.S. PATENT DOCUMENTS

| | | |
|---|---|---|
| 5,133,755 A | 7/1992 | Brekke |
| 5,366,508 A | 11/1994 | Brekke |
| 5,645,591 A | 7/1997 | Kuberasampath et al. |
| 5,683,459 A | 11/1997 | Brekke |
| 5,755,792 A | 5/1998 | Brekke |
| 5,769,899 A | 6/1998 | Schwartz et al. |

OTHER PUBLICATIONS

Kubler et al., "Bone morphogentic protein–mediated . . . ," Clinical Orthopaedics and Related Research, No. 258, pp. 279–294, (Sep. 1990).

*Primary Examiner*—James O. Wilson

(57) ABSTRACT

A bone growth-promoting composition is provided comprising hyaluronic acid and a growth factor. The composition has a viscosity and biodegradability sufficient to persist at the site of desired bone growth for a period of time sufficient to promote the bone growth. Preferably hyaluronic acid is used in a composition range of 0.1–4% by weight and preferred growth factor is bFGF, present in a concentration range of about $10^{-6}$ to 100 mg/ml.

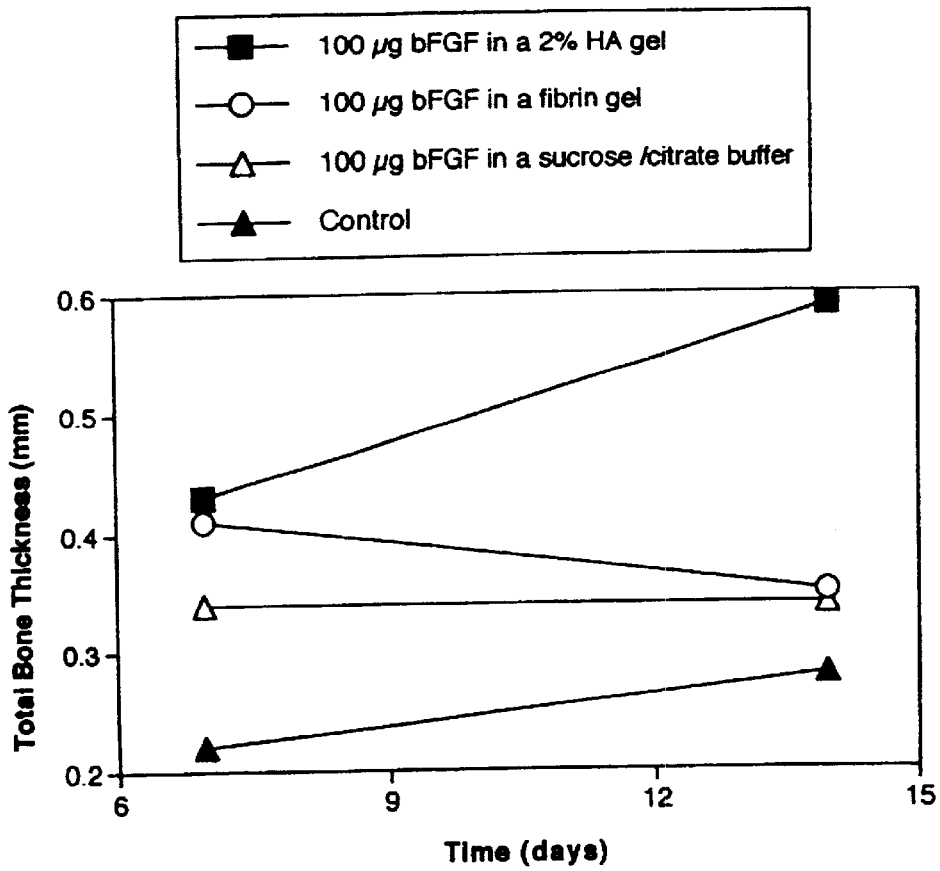

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 6 are determined to be patentable as amended.

Claims 2–5 and 7–10, dependent on an amended claim, are determined to be patentable.

1. A composition for treatment of diseased, injured or abnormal bone comprising an effective amount of [a] *an injectable* mixture of a growth factor and hyaluronic acid sufficient to enhance bone growth rate and magnitude [and], *said mixture* having [a] sufficient viscosity and biodegradability to persist upon application at an orthotopic or intraosseous site of desired bone growth for a period of time sufficient to enhance said bone growth rate and magnitude.

6. A method of treating diseased, injured or abnormal bone at an orthotopic or intraosseous site of desired bone growth comprising the step of applying to said site a composition comprising an effective amount of [a] *an injectable* mixture of hyaluronic acid and a growth factor sufficient to enhance bone growth rate and magnitude [and], *said mixture* having [a] sufficient viscosity and biodegradability to persist at said site for a period of time sufficient to enhance said bone growth rate and magnitude.

* * * * *